US008754776B2

(12) United States Patent  (10) Patent No.: US 8,754,776 B2
Poeze et al.  (45) Date of Patent: Jun. 17, 2014

(54) INTERFERENCE DETECTOR FOR PATIENT MONITOR

(71) Applicant: Cercacor Laboratories, Inc., Irvine, CA (US)

(72) Inventors: Jeroen Poeze, Mission Viejo, CA (US); Jesse Chen, Lake Forest, CA (US); Mathew Paul, Irvine, CA (US); Marcelo Lamego, Coto de Caza, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 13/918,206

(22) Filed: Jun. 14, 2013

(65) Prior Publication Data

US 2013/0278430 A1 Oct. 24, 2013

Related U.S. Application Data

(63) Continuation of application No. 12/841,965, filed on Jul. 22, 2010, now Pat. No. 8,471,713.

(60) Provisional application No. 61/228,495, filed on Jul. 24, 2009.

(51) Int. Cl.
*G08B 21/00* (2006.01)

(52) U.S. Cl.
USPC ........ 340/635; 340/573.1; 340/679; 340/3.43

(58) Field of Classification Search
USPC ................ 340/635, 573.1, 679, 691.1, 691.6, 340/3.43, 815.45, 815.46; 324/613; 600/504, 507, 483, 585, 500, 323; 128/900
See application file for complete search history.

(56) References Cited

U.S. PATENT DOCUMENTS

| 4,960,128 A | 10/1990 | Gordon et al. |
| 4,964,408 A | 10/1990 | Hink et al. |
| 5,041,187 A | 8/1991 | Hink et al. |

(Continued)

FOREIGN PATENT DOCUMENTS

WO  WO 2008/141306  11/2008

OTHER PUBLICATIONS

International Search Report and Written Opinion of the International Searching Authority issued in Application No. PCT/US2010/043120, mailed Oct. 27, 2010 in 15 pages.

*Primary Examiner* — Toan N Pham
(74) *Attorney, Agent, or Firm* — Knobbe, Martens, Olson & Bear LLP

(57) ABSTRACT

A system is disclosed for detecting and calculating the level of ambient and/or environmental noise, such as electromagnetic interference generated by electric power lines, ambient lights, light dimmers, television or computer displays, power supplies or transformers, and medical equipment. In some embodiments, the system performs frequency analysis on the interference signal detected by light photodetectors and determines the power of the interference signal concentrated in the analyzed frequency bands. The worst-case interference level can be determined by selecting the maximum from the computed power values. In some embodiments, the determined interference signal power can be compared with the noise tolerance of a patient monitoring system configured to reliably and non-invasively detect physiological parameters of a user. The results of the comparison can be presented to the user audio-visually. In some embodiments, the system can be used to perform spot check measurements of electromagnetic interference.

22 Claims, 10 Drawing Sheets

(56) References Cited

U.S. PATENT DOCUMENTS

| | | | |
|---|---|---|---|
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A * | 8/1998 | Flaherty et al. | 600/485 |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 * | 12/2003 | Kianl et al. | 600/322 |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |

(56) References Cited

U.S. PATENT DOCUMENTS

| | | | |
|---|---|---|---|
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |
| 7,377,899 | B2 | 5/2008 | Weber et al. |
| 7,383,070 | B2 | 6/2008 | Diab et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,526,328 | B2 | 4/2009 | Diab et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,572,230 | B2 * | 8/2009 | Neumann et al. ............ 600/504 |
| 7,596,398 | B2 | 9/2009 | Al-Ali et al. |
| 7,618,375 | B2 | 11/2009 | Flaherty et al. |
| D606,659 | S | 12/2009 | Kiani et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| RE41,317 | E | 5/2010 | Parker |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| 2007/0043269 | A1 | 2/2007 | Mannheimer et al. |
| 2009/0156924 | A1 | 6/2009 | Shariati et al. |
| 2011/0109459 | A1 | 5/2011 | Poeze et al. |

\* cited by examiner

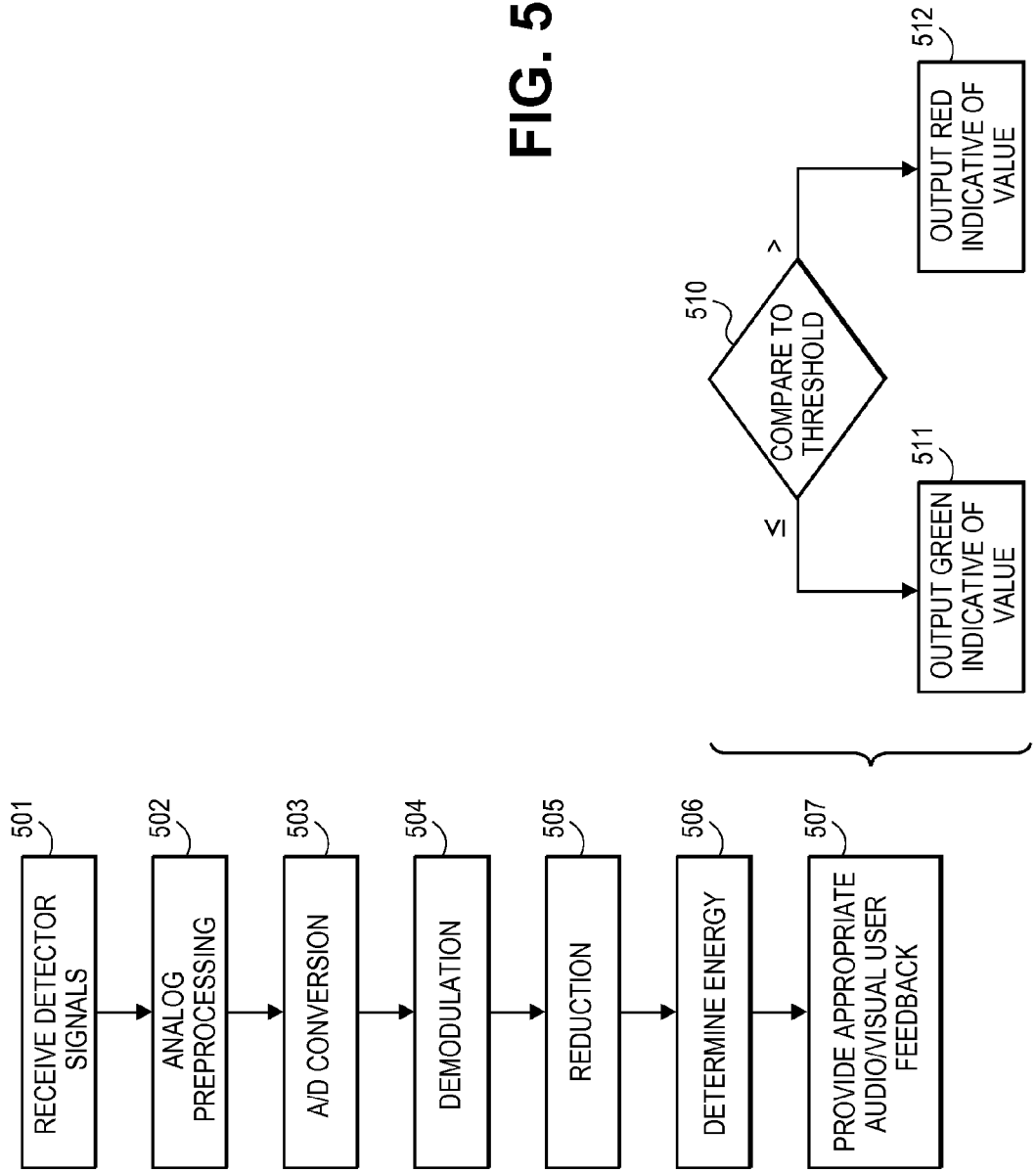

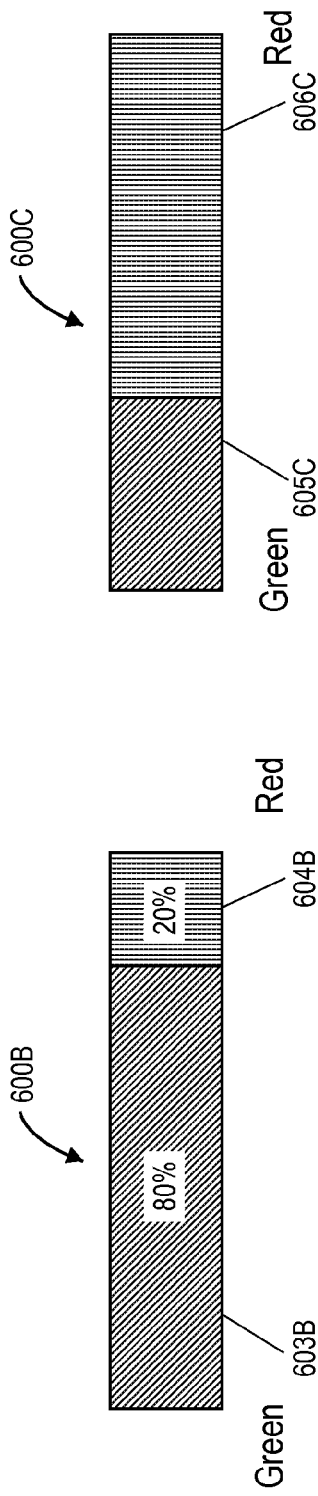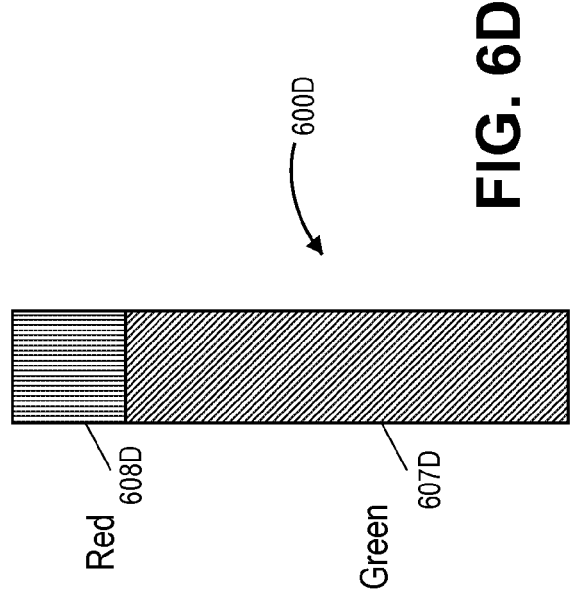
FIG. 6B
FIG. 6C
FIG. 6D

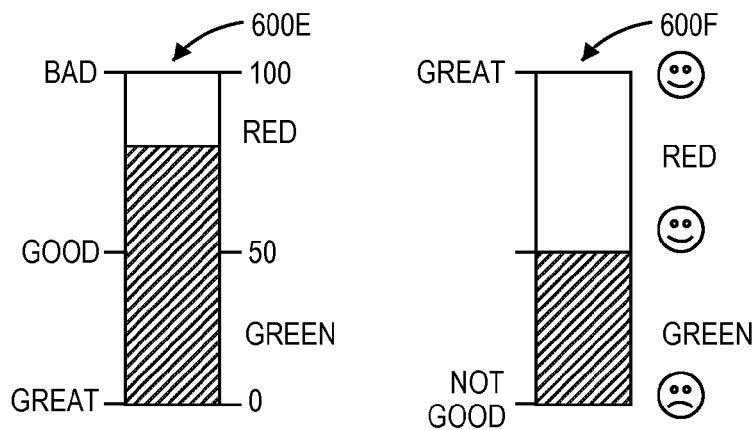
FIG. 6E  FIG. 6F
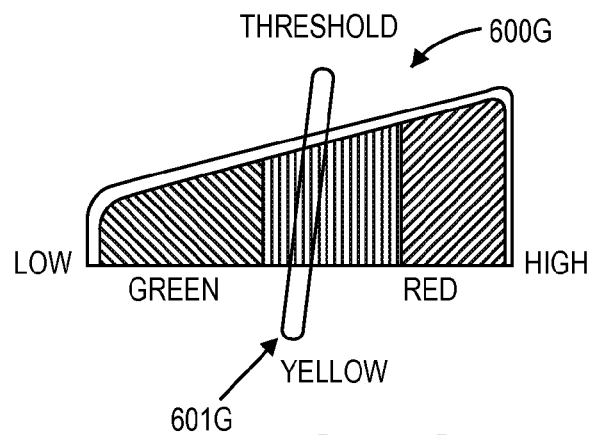
FIG. 6G
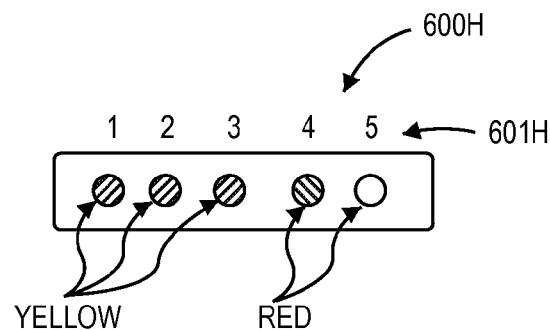
FIG. 6H

INTERFERENCE DETECTOR FOR PATIENT MONITOR

REFERENCE TO RELATED APPLICATIONS

The present application is a continuation of U.S. patent application Ser. No. 12/841,965, filed Jul. 22, 2010, entitled "Interference Detector for Patient Monitor," which claims priority benefit from U.S. Provisional Application No. 61/228,495, filed Jul. 24, 2009, entitled "Interference Detector for Patient Monitor," both of which are incorporated herein by reference.

The present application is related to U.S. Pat. No. 5,919,134, filed Jan. 12, 1998, entitled "Method and Apparatus for Demodulating Signals in Pulse Oximetry Systems"; and U.S. Pat. No. 6,526,300, filed Jun. 16, 2000, entitled "Pulse Oximeter Probe-Off Detection System, both of which are incorporated herein by reference.

BACKGROUND OF THE INVENTION

The present disclosure relates in general to patient monitoring systems including a patient monitor, one or more optical sensors, and a communication cable or device transferring signals between the monitor and the sensor(s).

Standard of care in caregiver environments includes patient monitoring through spectroscopic analysis using, for example, oximeter technologies commercially available from Masimo Corporation of Irvine. Devices capable of spectroscopic analysis generally include light sources transmitting optical radiation into a measurement site, such as, body tissue carrying pulsing blood. After attenuation (e.g. via transmission through tissue, reflectance, etc.) by tissue and fluids of the measurement site, one or more photodetection devices detects the attenuated light and outputs one or more detector signals responsive to the detected attenuated light. One or more signal processing devices process the detector(s) signal(s) and output a measurement indicative of a blood constituent of interest, such as, glucose, oxygen, methemoglobin, total hemoglobin, other physiological parameters, or other data or combinations of data useful in determining a state or trend of wellness of a patient. Such combinations often include statistical analysis of one or more measurements or combinations of different parameter measurements into useful information.

In addition to the foregoing, considerable efforts have been made to develop noninvasive oximeter techniques for measuring other blood analytes or patient parameters, including for example, glucose, total hemoglobin, or the like. Unfortunately, some of these parameters have proven to be difficult to measure using noninvasive spectroscopy. For example, the biologic tissue and water of a measurement site have a high intrinsic absorption at many of the wavelengths of light that are useful in measuring blood glucose. Moreover, blood glucose exists in relatively low concentrations comparatively with other blood analytes. Furthermore, different patients will have large variations in the optical properties of their skin and blood composition.

Moreover, ambient and/or environment interference (i.e., noise) can adversely affect the measurement accuracy. Interference is generated by many commonly-used electrical devices. In a typical household for example, electric power lines and outlets, ambient lights, light dimmers, television or computer displays, and power supplies or transformers generate electromagnetic interference. For example, noise caused by ambient light will generally vary with a periodicity corresponding to a 50 Hz or 60 Hz fundamental frequency and its harmonics. As will be understood by those of skill in the art, the ambient light frequency is a function of the frequency of electricity powering the ambient lights and other interfering devices and/or the frequency of naturally occurring light. The ambient light frequency will, accordingly, change depending on the power system used to operate the devices creating the ambient light. Harmonics of the fundamental ambient light frequency are important because the ambient light can still cause significant interference at the harmonic frequencies. This is particularly true when the ambient light is provided by fluorescent lights which generate significant noise at the second harmonic (i.e., 100 Hz or 120 Hz) and the fourth harmonic (i.e., 200 Hz or 240 Hz). In addition in typical care environments medical equipment (e.g., electrocauterization devices) also generates significant electromagnetic interference. These and other challenges make signal information indicative of physiological parameters (e.g., glucose) difficult to differentiate from the interference signal. Moreover, patients and other users often desire glucose and other physiological parameter data in at least spot check measurements in a wide variety of care and non-care environments where interference levels are unknown.

SUMMARY OF THE INVENTION

In some embodiments of the present disclosure, an interference detector configured to reliably measure the levels of ambient and/or environment interference is described. The detector utilizes frequency analysis to determine and calculate interference levels in the frequency bands of interest. Such bands of interest can be configured to be those frequencies used for analysis during measuring the various physiological parameters. For example, a modulated light signal attenuated by body tissue or fluids can comprise physiological information at the fundamental frequency and harmonic frequencies of the carrier signal (e.g., a periodic pulse train). Interference levels can be measured at the fundamental frequency and harmonic frequencies to determine the likelihood of obtaining reliable measurements of physiological parameters in the presence of ambient and/or environment noise.

In some embodiments of the present disclosure, the interference levels can be computed as energy or power of interference signals concentrated at the frequencies of interest. The maximum measured power can be used to determine the worst-case effect of ambient and/or environmental interference on the accuracy of measurements of physiological parameters. This maximum measured power can be compared with a threshold to obtain an objective determination of the significance of the interference and its expected degradation of the accuracy of the measurements. The threshold can be selected as a multiple of the noise floor of the interference detector or, in other words, the measured noise signal that is inherently present in the system because of thermal noise, shot noise, and the like. The noise floor further establishes a limit on the smallest measurement that can be reliably preformed by the system. The multiple of the noise floor and the threshold can be varied depending on the type of physiological parameter being measured by the device.

In some embodiments of the present disclosure, the interference detector can be configured to provide audio-visual indication of the measured interference levels, relative to the threshold, to the user. Visual indication can comprise displaying bar graphs, charts, graphs, and the like of the measured, relative interference levels. Audio indication can comprise speaking the severity of the measured, relative interference levels. Audio-visual indication can be helpful in spot check measurement situations because the user can be quickly informed as to the expected accuracy of the measurement of physiological parameters. In addition, the user can be quickly alerted in situations where ambient and/or environmental interference can significantly degrade the measurement accuracy or cause the measurements be unreliable.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIG. 5 illustrates an interference detection process, according to an embodiment of the disclosure.

FIGS. 6A-H illustrate exemplary user interface indicia indicating use of and output from the interference detector of FIG. 1.

DETAILED DESCRIPTION OF THE PREFERRED EMBODIMENT

Figure 1:
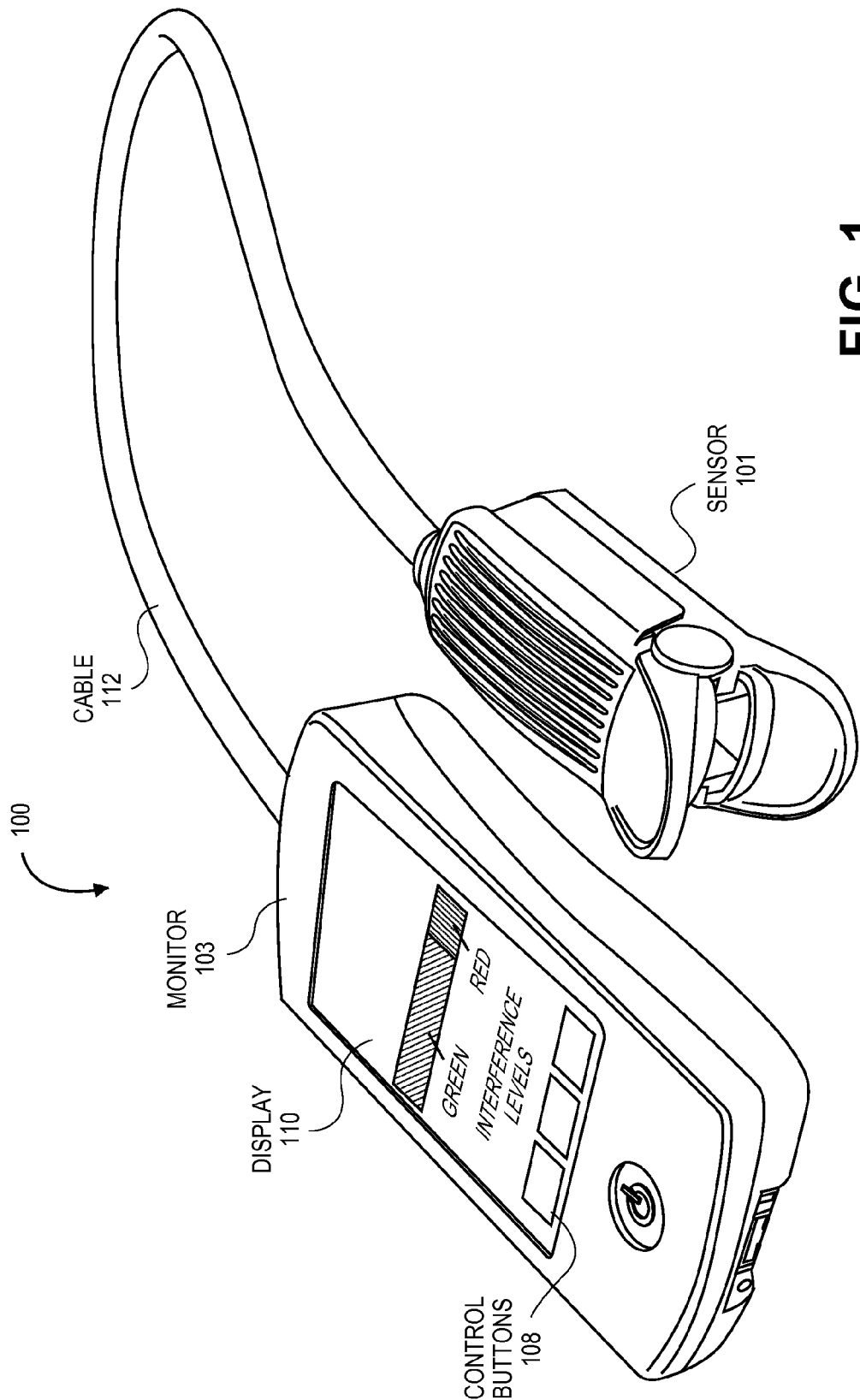
FIG. 1 illustrates a perspective view of an exemplary patient monitoring system including exemplary visual indicia of an output of an interference detector, according to an embodiment of the disclosure.

Ambient and/or environment interference (i.e., noise) can adversely affect the measurement accuracy of non-invasive patient monitoring systems, such as systems capable of measuring glucose, oxygen, methemoglobin, total hemoglobin, and other physiological parameters. To perform the measurements, these systems typically utilize signal processing analysis of optical radiation (e.g., light) signal detected by photodetectors after it has been attenuated by body tissue and fluids. However, significant interference is generated by many commonly-used electrical devices, such as electric power lines and outlets, ambient lights, light dimmers, television or computer displays, power supplies or transformers, and medical equipment (e.g., electrocauterization devices). It can be difficult to differentiate signal information indicative of physiological parameters from the interference. Moreover, patients and other users often desire glucose and other physiological parameter data in at least spot check measurements in a wide variety of care and non-care environments where the interference levels are unknown.

Existing solutions for measuring the interference levels can be inadequate, especially in spot check situations. For example, one approach is to measure the interference at the same time as performing measurements of physiological parameters. However, this can be unreliable because interference may be highly non-stationary and non-periodic, may have short-duration components with significant energy levels, and so on. Accordingly, such measurements of interference levels can be inaccurate and unreliable.

In some embodiments of the present disclosure, an interference detector configured to reliably measure the interference levels is described. The detector utilizes frequency analysis to determine and calculate interference levels in the frequency bands of interest. Such bands of interest can be configured to be those frequencies used for analysis during measuring the various physiological parameters. For example, a modulated light signal attenuated by body tissue or fluids can comprise physiological information at the fundamental frequency and harmonic frequencies of the carrier signal (e.g., a periodic pulse train). Interference levels can be measured at the fundamental frequency and harmonic frequencies to determine the likelihood of obtaining reliable measurements of physiological parameters in the presence of ambient and/or environment noise. In some embodiments, the interference levels can be used to determine a best modulation rate that will result in the least interference to the desired signal.

In some embodiments of the present disclosure, the interference levels can be computed as energy or power of interference signals concentrated at the frequencies of interest. The maximum measured power can be used to determine the worst-case effect of ambient and/or environmental interference on the accuracy of measurements of physiological parameters. This maximum measured power can be compared with a threshold to obtain an objective determination of the significance of the interference and its expected degradation of the accuracy of the measurements. The threshold can be selected as a multiple of the noise floor of the interference detector or, in other words, the measured noise signal that is inherently present in the system because of thermal noise, shot noise, and the like. The noise floor further establishes a limit on the smallest measurement that can be reliably performed by the system. The multiple of the noise floor and the threshold can be varied depending on the type of physiological parameter being measured by the device.

In some embodiments of the present disclosure, the interference detector can be configured to provide audio-visual indication of the measured interference levels, relative to the threshold, to the user. Visual indication can comprise displaying bar graphs, charts, graphs, and the like of the measured, relative interference levels. Audio indication can comprise speaking the severity of the measured, relative interference levels. Audio-visual indication can be helpful in spot check measurement situations because the user can be quickly informed as to the expected accuracy of the measurement of physiological parameters. In addition, the user can be quickly alerted in situations where ambient and/or environmental interference can significantly degrade the measurement accuracy or cause the measurements be unreliable.

To facilitate a complete understanding of the invention, the remainder of the detailed description describes the invention with reference to the drawings, wherein like reference numbers are referenced with like numerals throughout.

FIG. 1 illustrates a perspective view of a patient monitoring system 100, according to an embodiment of the disclosure. The system 100 includes a portable patient monitor 103 capable of noninvasively determining one or more psychological parameters and also interference levels. The portable patient monitor 103 communicates with an optical sensor 101 through a cable 112. In some embodiments, the patient monitor 103 drives the sensor 101 to emit light of different wavelength into a body tissue (not shown). The sensor 101 detects the light after attenuation by the body tissue and outputs a signal indicative of the amount of light received by the sensor 101 (which can include attenuation) through the cable 112. In addition, in some embodiments, the monitor 103 communicates with a temperature sensor and a memory device associated with one or more of the sensor 101 and the cable 112, through the cable 112. In some embodiments, the monitor 103 communicates with other storage devices and remote devices via a network interface (not shown).

The patient monitor can comprise a display 110 and one or more control buttons 108. In some embodiments, the display 110 can be a touch sensitive display that can include one or more virtual controls and/or changing display and/or control screens. The display 110 can be configured to display a wide variety of measured psychological parameters in a manner that provides for quick and efficient conveyance of information to a user. For example, the display 110 can show values for blood oxygen saturation, pulse, glucose, methemoglobin, total hemoglobin, and the like. In addition, as shown in FIG. 1, the display 110 can convey visual indicia of the detected noise interference levels. For example, the display 110 can be configured to output a bar graph where, as explained in more detail below, green shading corresponds to low level interference levels and red shading corresponds to high interference levels.

Figure 2:
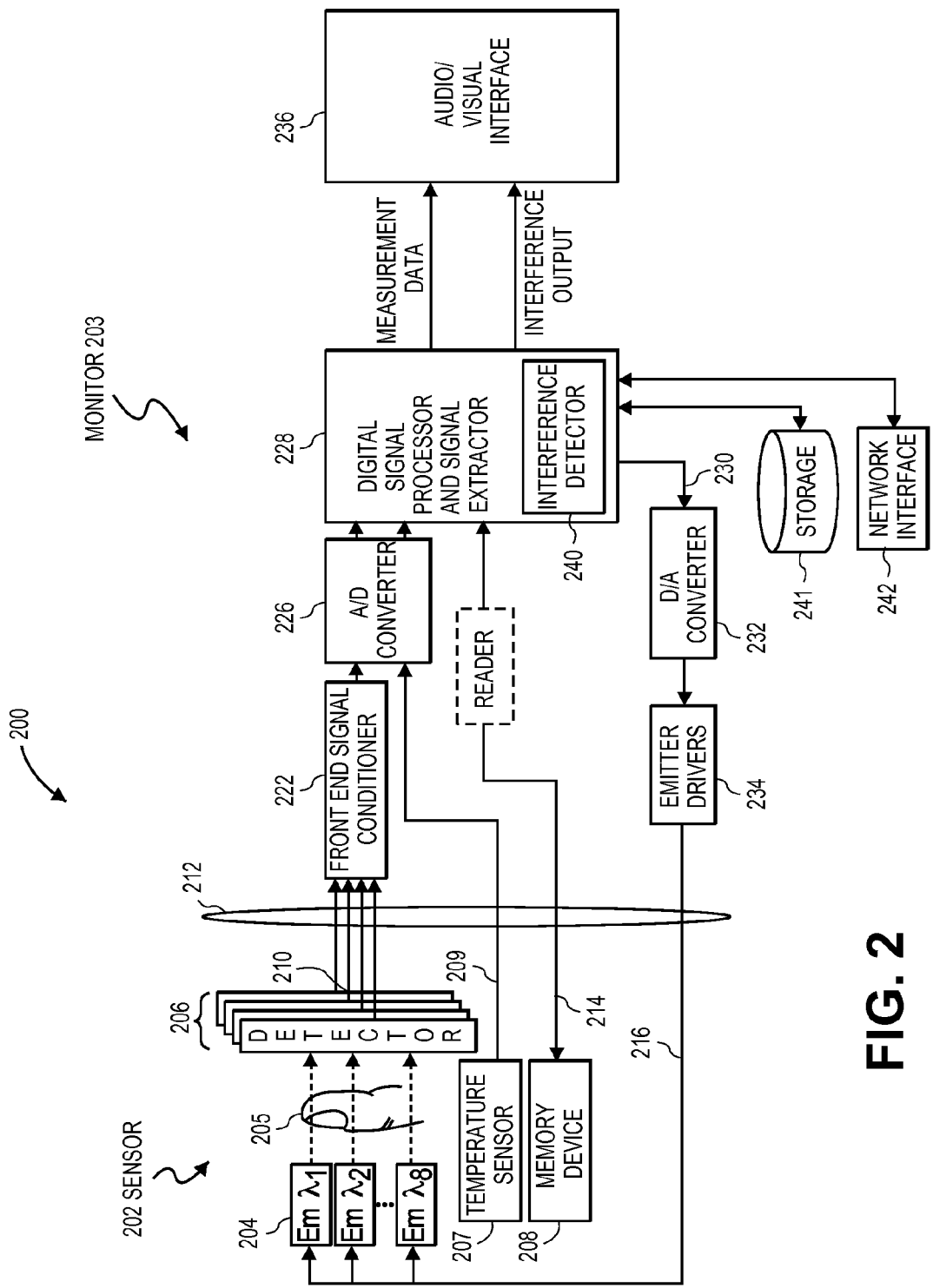
FIG. 2 illustrates an exemplary block diagram of a patient monitor and the interference detector of the patient monitoring system of FIG. 1.

FIG. 2 illustrates a block diagram of a patient monitor and interference detector of the patient monitoring system 200, such as, for example, the monitoring system 100 of FIG. 1. As shown in FIG. 2, the monitoring system 200 includes a sensor 202 and a patient monitor 203, communicating through a cable 212. In some embodiments, the sensor 202 includes a plurality of emitters 204 (e.g., eight emitters as is shown in FIG. 1) irradiating a body tissue 205 with light and one or more detectors 206 (e.g., four detectors as shown in FIG. 2) capable of detecting light after attenuation by the tissue 205. In some embodiments, the sensor 202 can be configured such that one or more detectors 206 detect ambient and/or environment interference levels after attenuation by the tissue 205.

The sensor 202 can additionally comprise a temperature sensor 207, such as a thermistor or a thermocouple, and a memory device 208, such non-volatile (e.g., an EEPROM) or volatile memory. The sensor 202 also includes a plurality of conductors communicating signals to and from its components, including temperature sensor conductors 209, detector composite signal conductors 210, memory device conductors 214, and emitter drive signal conductors 216. In some embodiments, the sensor conductors 209, 210, 214, 216 communicate their signals to the monitor 203 through the cable 212. In some embodiments, the cable 212 includes a plurality of shielded conductors.

Although disclosed with reference to the cable 212, a skilled artisan will recognize from the disclosure herein that the communication to and from the sensor 202 may advantageously include a wide variety of cables, cable designs, public or private communication networks or computing systems, wired or wireless communications (such as Ethernet, Bluetooth or WiFi, including IEEE 802.11x), mobile communications, combinations of the same, or the like.

In some embodiments, the temperature sensor 207 monitors the temperature of the sensor 202 and its components, such as, for, example, the emitters 204. For example, in some embodiments, the temperature sensor 207 comprises or communicates with a thermal bulk mass having sufficient thermal conduction to generally approximate a real-time temperature of a substrate of the light emitters 204. In some embodiments, the monitor 203 may advantageously use the temperature sensor 207 output to, among other things, ensure patient safety, especially in applications with sensitive tissue 205. In some embodiments, the monitor 203 may advantageously use the temperature sensor 207 output and monitored operating current or voltages to correct for operating conditions of the sensor 202.

The memory 208 can comprise any one or more of a wide variety of memory devices known to a skilled artisan from the disclosure herein, including non-volatile memory, volatile memory, or combination thereof. The memory 208 can be configured to store some or all of a wide variety data and information, including, for example, information on the type or operation of the sensor 202, type of patient or body tissue 205, buyer or manufacturer information, sensor characteristics including the number of wavelengths capable of being emitted, emitter specifications, emitter drive requirements, demodulation data, calculation mode data, calibration data, software or firmware such as scripts, executable code, or the like, sensor electronic elements, sensor life data indicating whether some or all sensor components have expired and should be replaced, encryption information, monitor or algorithm upgrade instructions or data, or the like. In some embodiments, the memory device 208 may also include emitter wavelength correction data. In some embodiments, the monitor 203 can read the memory 208 to determine one, some or all of a wide variety of data and information stored. As is shown In FIG. 2, a digital signal processor 228 can communicate with the memory device 208, by using a memory reader, memory writer, or the like.

The monitor 203 can comprise a front end signal conditioner 222 configured to receive, through the conductors 210, the analog composite detector signal from the detectors 206. The signal conditioner 222 can normalize the analog composite detector signal by adjusting the signal's gain, remove unwanted frequency components by passing the signal through a band-pass or a low-pass filter, normalize the phase of the signal by passing it through an all-pass filter with the desired phase response, and the like. The signal conditioner 222 includes one or more outputs communicating with an analog-to-digital converter 226 ("A/D converter"). In some embodiments, the A/D converter 226 may comprise a delta-sigma converter to provide better linearity and signal-to-noise performance, which, among other things, advantageously enhances measurements during lower perfusion. The reduced signal-to-noise may also improve measurement quality by providing better rejection of ambient and/or environment interference (e.g., from electrocauterization devices). The A/D converter 226 includes inputs communicating with the output of the front end signal conditioner 222 and the output of the temperature sensor 207. The converter 226 also includes outputs for communicating the digitized composite detector signal values and temperature sensor readings to the processor 228.

The processor 228 can output an emitter driver current control signal 230 to a digital-to-analog converter 232 ("D/A converter"). The D/A converter 232 can supply control information to emitter driving circuitry 234, which in turns drives the plurality of emitters 204 on the sensor 202 over conductors 216. In some embodiments, the emitter driving circuitry 234 drives eight emitters capable of emitting light at eight predefined wavelengths, although the circuitry 234 can drive any number of emitters. In addition, one or more emitters could emit light at the same or substantially the same wavelength to provide redundancy. The circuitry 234 can be configured to modulate the emitters 204, by turning them on and off, as to produce pulse trains of light at the corresponding wavelengths. In some embodiments, the circuitry 234 can be configured to turn the emitters 204 off as to cause the detectors 206 to detect the level of ambient or environment noise, which can additionally modulate by the rectangular pulse train carrier signal. Further details of modulation are disclosed in U.S. Pat. No. 6,229,856, issued on May 8, 2001, the disclosure of which is incorporated by reference herein.

The processor 228 can process digitized composite detector signal values and calculate physiological parameter information, such as blood oxygen saturation, pulse, glucose, methemoglobin, total hemoglobin, and the like. The processor 228 comprises an interference detector 240 configured to calculate the levels of ambient and/or environment interference comprised in the composite detector signal. In some embodiments, the processor 228 can read the information stored in the memory device 208 and use the retrieved information for calculation of physiological parameter information and/or interference levels.

The processor 228 can communicate with the audio/visual interface 236, for example, to display the measured and calculated parameters or interference levels.

The audio/visual interface 236 can be configured as a display device capable of providing indicia representative of the calculated physiological parameters of the tissue 205 at the measurement site and of the calculated interference levels. In some embodiments, the audio/visual interface 236 can display trending data for one or more of the measured or determined parameters or interference levels. Moreover, an artisan will recognize from the disclosure herein many display options for the data available from the processor 228.

In addition, the processor 228 can communicate with local and/or remote storage 241 and local and/or remote network devices through network interface 242. Storage 241 can be configured as non-volatile memory, volatile memory or combination thereof. Storage 241 can be in the form of a hard disk, flash memory card, or other suitable computer accessible memory. In some embodiments, the processor 228 can store a variety of information in the storage 241, such as calculated physiological parameter information and interference levels. This information can be later retrieved and used in future calculations. In some embodiments, the processor can communicate variety of information to network devices over the network interface 242. The network interface 242 can be configured with a wide variety of cables, cable designs, public or private communication networks or computing systems, wired or wireless communications (such as Ethernet, Bluetooth or WiFi, including IEEE 802.11x), mobile communications, combinations of the same, or the like. The processor 228 can exchange a variety of information with network devices, such as calculated physiological parameter information and interference levels.

Figure 3:
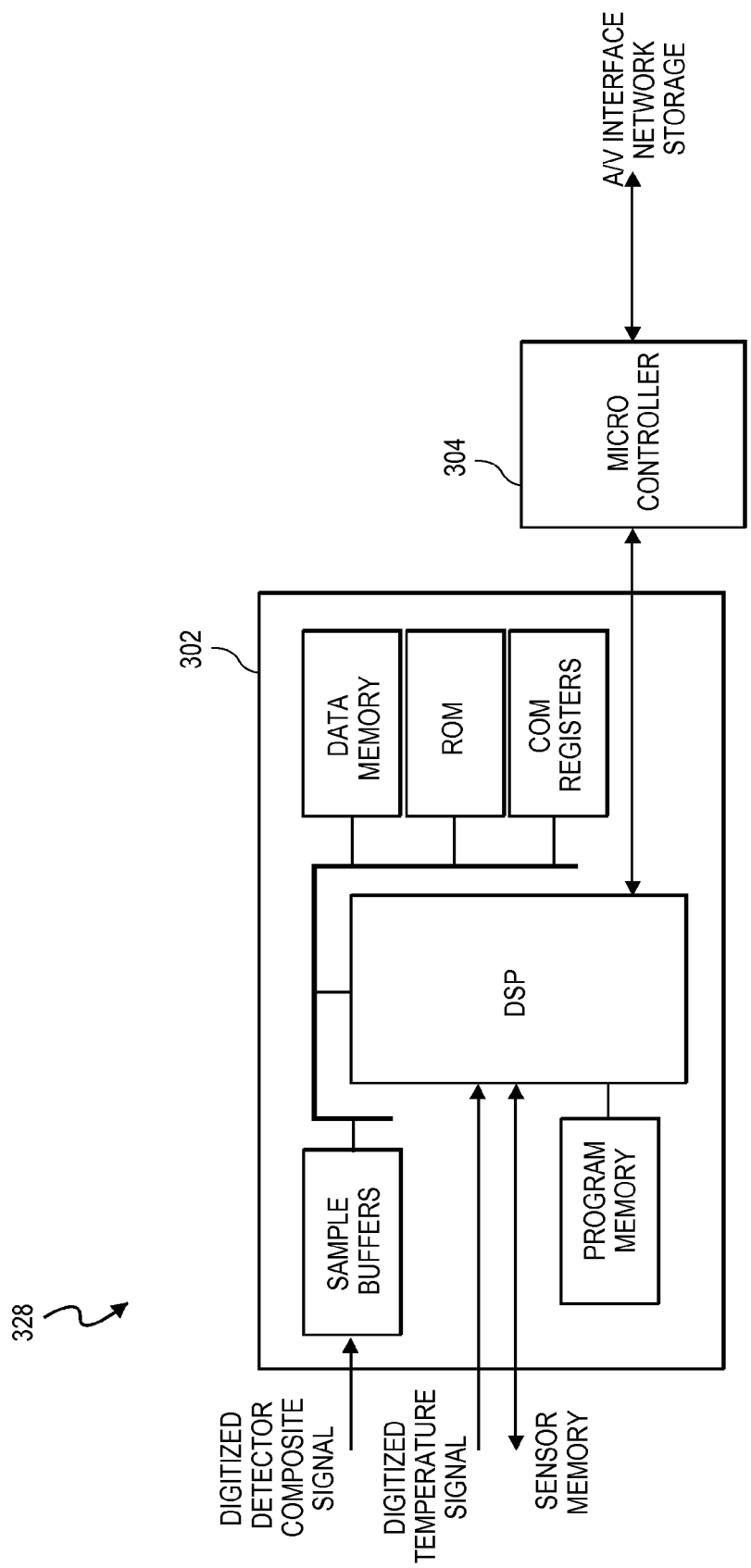
FIG. 3 illustrates an exemplary hardware block diagram of a digital signal processor and signal extractor of the patient monitor of FIG. 2.

FIG. 3 illustrates a hardware block diagram of a digital signal processor and signal extractor 328 of the patient monitor, such as, for example, the processor 228 of FIG. 2. As shown in FIG. 3, the processor 328 can comprise a core processor 302 and a microcontroller 304. According to some embodiments, the core processor can comprise a digital signal processor based on the Super Harvard ARChitecture ("SHARC"), such as those commercially available from Analog Devices. FIG. 3 shows various exemplary component details of typical SHARC processors. However, a skilled artisan will recognize from the disclosure herein a wide variety of data and/or signal processors capable of executing programs for determining physiological parameters from input data, preferably a digital signal processor that can handle at least 16, 32, or 40 bits of floating point or fixed point for precision. According to some embodiments, the microcontroller 304 controls system management, including, for example, communications of calculated parameter data, interference levels, and the like to an audio/visual interface; communication of information to an from remote or local network devices or storage; and the like. In some embodiments, the microcontroller 304 may also act as a watchdog circuit by, for example, monitoring the activity of the core processor 302 and resetting it when appropriate.

Figure 4A:
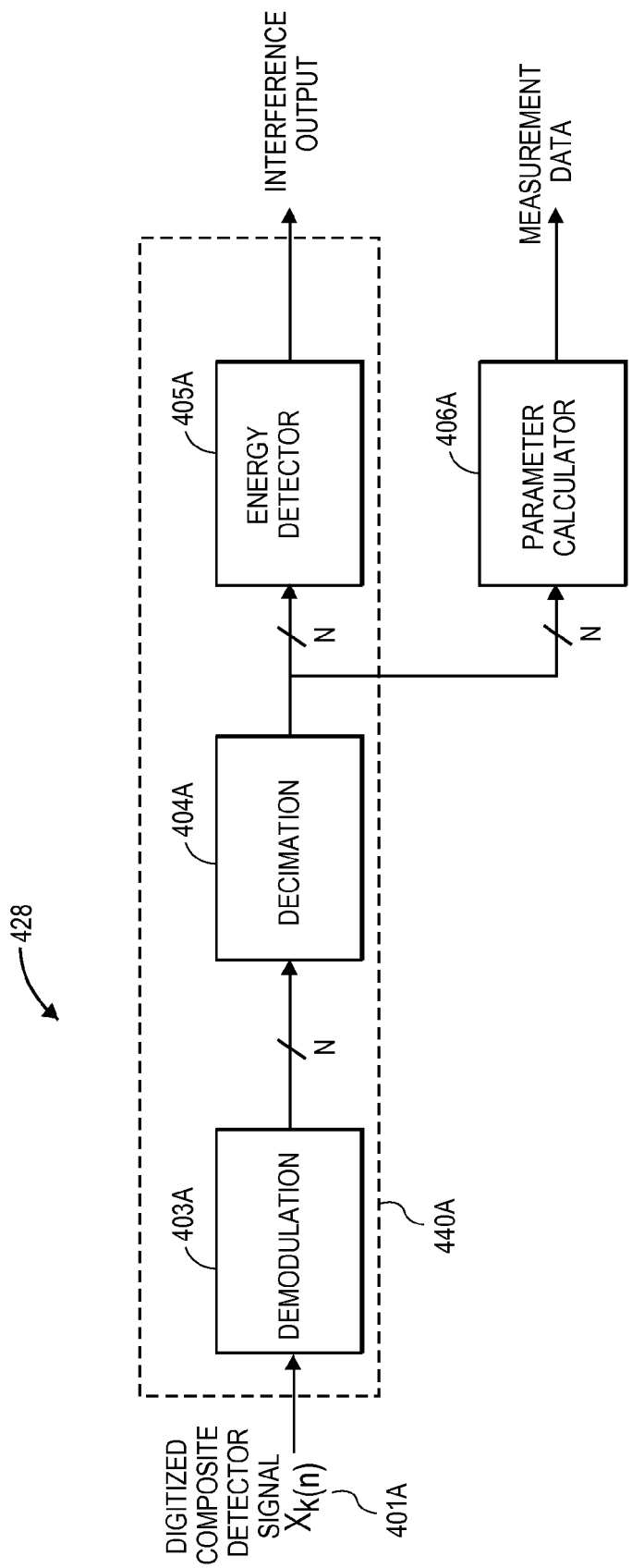
FIG. 4A-C illustrate exemplary functional block diagrams of a digital signal processor and signal extractor and interference detector of the patient monitor of FIG. 2.

FIG. 4A illustrates a functional block diagram of a digital signal processor and interference detector 428 of the patient monitor, such as, for example, the processor 228 of FIG. 2. As is shown in FIG. 4A, the input to the processor and interference detector 428 can be a digitized composite detector signal $x_k(n)$ 401A. In some embodiments, the digitized composite detector signal 401A, $x_k(n)$, can represent digitized samples of a signal from a single detector 206 (i.e., k can correspond to the number of detectors 206) and a separate signal processing, modeling, and computation path as shown in FIG. 4A can be used for each signal $x_k(n)$. In some embodiments, the composite detector signal 401A can comprise the interference signal detected by the detectors 206, without any light data.

In some embodiments a demodulation module 403A models and demodulates the digitized composite detector signal 401A (e.g., a 48 KHz composite signal) to separate the composite signal into signals related to each emitted wavelength and to remove the frequency components of the carrier signal. In addition, the demodulation module 403A can be configured to model and demodulate the digitized composite detector signal to separate the interference signal into interference signals related to each emitted wavelength and to remove the frequency components of the carrier signal. In some embodiments the demodulation module 403A can be configured to model and demodulate digitized composite detector signal data into N (e.g., 8) channels of demodulated data. Each channel can be configured to correspond to a different frequency and/or phase characteristics. For example, each channel can correspond to a fundamental frequency and its harmonics of the rectangular light pulse train carrier signal modulated by the light signal emitted by an emitter 204. Furthermore, as explained below, several channels can share the same frequency characteristic, and, in such embodiments, phase can be used to distinguish these channels.

The multiple channels of demodulated data samples can be presented to a decimation module 404A, which is configured to reduce the sampling rate by eliminating samples and, additionally, may provide signal conditioning and filtering. Because decimation reduces the number of data samples, it can reduce computational burden on the digital signal processor and interference detector 428 and, additionally, reduce power consumption of the patient monitor. In some embodiments, a 48 KHz demodulated multiple channel data stream can be decimated to 62.5 Hz.

To determine the interference levels, the multiple channels of demodulated and decimated data can be presented to an energy detector 405A. In some embodiments, the composite detector signal $x_k(n)$ 401A can comprise only the interference signal, as the emitters 204 can be configured (e.g., by the circuitry 234) to be off. Then, the multiple channels of demodulated and decimated data comprise interference signals, and the energy detector 405A can be configured to compute the energy or power of the interference signals. In some embodiments, as is explained below, the energy detector 405A can compute the average power of the interference signal on each of the decimation channels and to select the maximum power value as the interference output.

To compute physiological parameter information, such as blood oxygen saturation, pulse, glucose, methemoglobin, total hemoglobin, and the like, the multiple channels of demodulated and decimated data can be presented to a parameter calculator 406A. The parameter calculator 406A can model, condition, and process the data according to various algorithms for computation of physiological information, as is described in U.S. application Ser. No. 11/367,017 (filed Mar. 1, 2006), the disclosure of which is incorporated by reference herein.

Figure 4B:
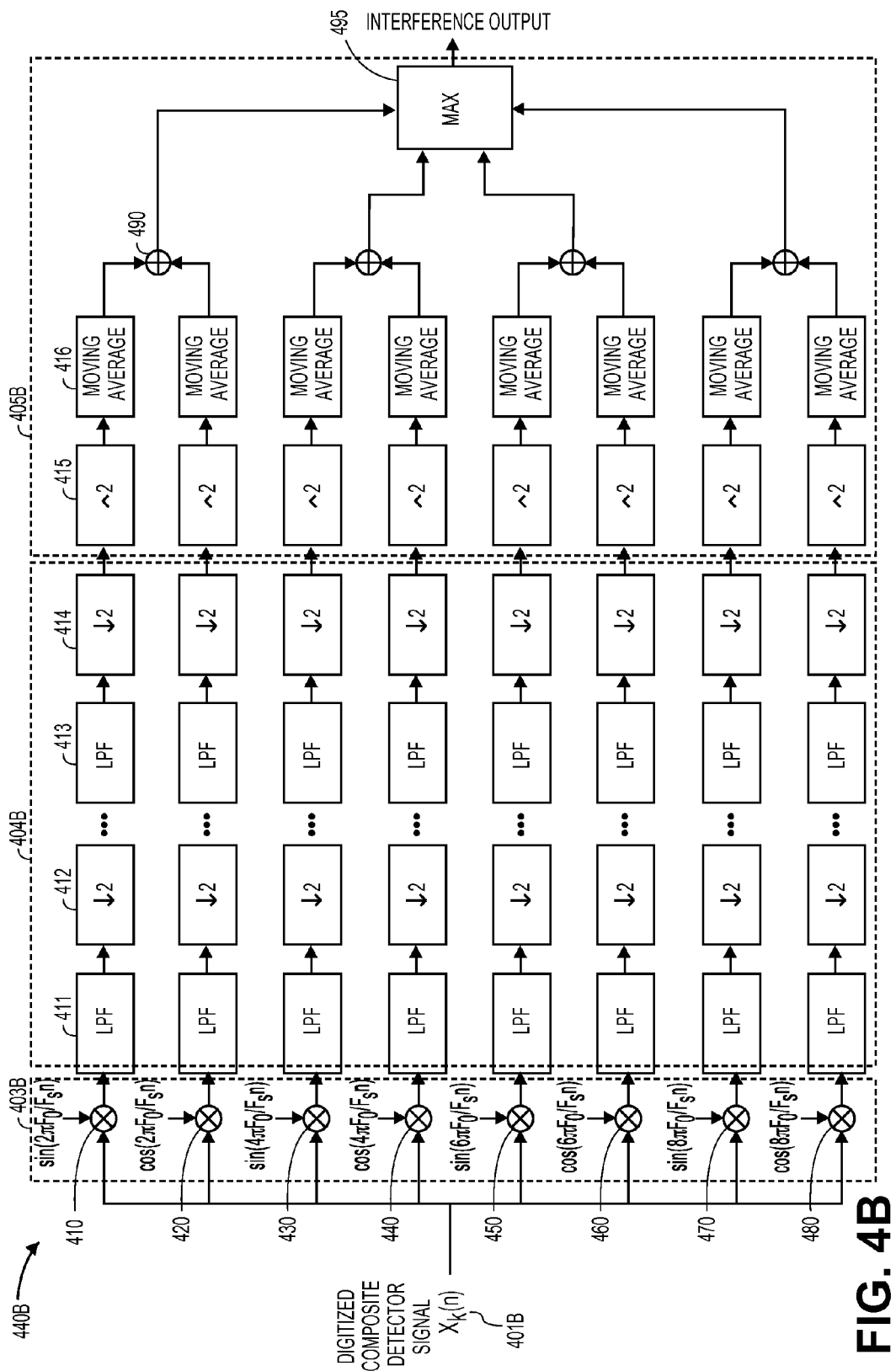

FIG. 4B illustrates a functional block diagram of an interference detector 440B of the patient monitor, such as, for example, the processor 428 of FIG. 4A. As is shown in FIG. 4B, the input to the interference detector 440B can be a digitized composite detector signal $x_k(n)$ 401B. In some embodiments, the digitized composite detector signal 401B, $x_k(n)$, can represent digitized samples of a signal from a single detector 206 (i.e., k can correspond to the number of detectors 206) and, as is explained below, a separate interference detector (such as the detector 440B) can be used for each signal $x_k(n)$. In some embodiments, the composite detector signal 401B can comprise the interference signal detected by the detectors 206, without any light data. This can be accomplished, for example, by configuring the circuitry 234 of FIG. 2 to keep the emitters 204 off and by configuring the detectors 206 to detect only the ambient and/or environment interference levels attenuated by the tissue 205.

A demodulation module 403B models and demodulates the digitized composite detector signal $x_k(n)$ 401B (e.g., a 48 KHz composite signal) to separate the interference signal into interference signals related to each emitted wavelength and to remove the frequency components of the carrier signal. As is illustrated in FIG. 4B, in some embodiments the demodulation module 403B can be configured to model and demodulate the digitized composite detector signal 401B into N (e.g., 8) channels of demodulated data. Each channel can be configured to correspond to a different frequency (i.e., sin(t) and cos(t) components of each harmonic, as is further explained below) of the modulated light signal produced by an emitter 204.

In some embodiments, a modulated light signal can be produced by modulating a periodic, rectangular pulse train (i.e., the carrier signal) by the light produced by the emitters 204. The circuit 234 can be configured such that only one emitter 204 (e.g., light emitting diodes) is active at any given time period. For example, if there are two emitters 204 (e.g., red and infrared light emitting diodes), the circuit 234 can apply current to activate the first emitter during a first time interval of duration $\tau_1$, while keeping the second emitter inactive. Thereafter, no current can be applied to either emitter during a second time interval of duration $\tau_2$. Then, the current can be applied to activate the second emitter during a third time interval of duration $\tau_3$, while keeping the first emitter inactive. Finally, the modulation cycle can be completed by applying no current to either emitter during a fourth time interval $\tau_4$. Thereafter, the cycle can be repeated by restarting with the first interval. All four time intervals $\tau_1, \tau_3, \tau_3,$ and $\tau_4$ can be of the same duration $\tau$. Accordingly, the carrier signal, a periodic, rectangular pulse train having a pulse width $\tau$ and a period of $4\tau$ and corresponding Fourier coefficients of $\tau F_0 * \sin c(kF_0\tau)$, where $F_0$ is the fundamental frequency (i.e. inverse of the period) and $k=\pm 1, \pm 2, \ldots$, is modulated by the light emitted by emitters 204. The Fourier coefficients correspond to the fundamental frequency and its harmonics (or integer multiples of the fundamental frequency). The circuit 234 can be configured to similarly modulate any number of carrier signals by any number of emitters 204, such as 8 emitters.

In order to recover the intensity of the light signal, attenuated through the tissue 205 and detected by the detectors 206, the demodulation module 403B can be configured to model and analyze the composite detector signal 401B at the fundamental frequency $F_0$ and the harmonics of the periodic pulse train ("frequencies of interest"). This can be accomplished by shifting the envelope of the modulated signal (i.e. composite detector signal), or part of the envelope that comprises a significant energy of the intensity signal, to a frequency of interest and then applying a filter to remove components at other higher frequencies. In some embodiments, several frequencies of interest can be used and shifting of the envelope can be accomplished by multiplying the modulated signal by a cosine or sine signal having the frequency corresponding to the frequency of interest. A skilled artisan will recognize from the disclosure herein that frequencies of interest can be frequencies other than the fundamental frequency $F_0$ and its harmonics and demodulations methods other than shifting the signal envelope can be used.

In some embodiments, the demodulation module 403B can be further configured to reduce or eliminate in the composite detector signal crosstalk between the light signals output by different emitters 204. For example, if there are two emitters 204 (e.g., red and infrared light emitting diode), crosstalk in the composite detector signal can be defined as the effect of the red light signal on the infrared light signal and vice versa. Such crosstalk can be minimized or eliminated by selecting appropriate demodulating signals and multiplying these by the composite detector signal. In some embodiments as is explained in the above-identified issued U.S. Pat. No. 6,229,856, demodulating signals reducing or eliminating crosstalk can be configured as cosine signals with frequencies of the fundamental frequency $F_0$ and harmonics of the carrier pulse train: $C_1 \cos(2\pi F_0 t), C_2 \cos(4\pi F_0 t), C_3 \cos(6\pi F_0 t)$, and so on (where $C_1, C_2, C_3, \ldots$ are constants selected to minimize or eliminate crosstalk).

Additionally, selecting frequencies of interest can result in reducing the effect of at least some types and intensities of ambient or environment noise on the light intensity signals. For example, the fundamental frequency $F_0$ can be selected as 316.7 Hz (i.e., with harmonics at 316.7 n Hz, where n is an integer value) to reduce or eliminate the effect of power line noise (60 Hz or 50 Hz fundamental frequency with harmonics at 60 n Hz or 50 n Hz, where n is an integer value). Accordingly, the nearest harmonic of power line noise to the light signal intensity comprised by the modulated pulse train having the fundamental frequency of 316.7 Hz would be 300 and 360 Hz, for 60 Hz power line frequency, and 300 and 350 Hz, for 50 Hz power line frequency. This would provide a frequency separation of noise and light intensity. In some embodiments, the fundamental frequency $F_0$ can be selected as 330 Hz to provide the separation.

Accordingly, in some embodiments, the demodulation module 403B of the interference detector 440B can be configured to model and analyze the composite detector signal 401B, which comprises interference, at the fundamental frequency $F_0$ and its harmonics. Accordingly, the demodulation module 403B operates at the modulation frequency and its harmonics as applied to demodulate the modulated composite light signal. As is explained above, interference signals having components at these frequencies of interest can significantly degrade the recovery of the light intensity signals from the composite detector signal. Therefore, it is advantageous to determine the level of interference at these frequencies of interest and to compute the likelihood of successful recovery and processing of the light intensity signals given in the presence of ambient and/or environment interference. In some embodiments, the demodulation module 403B can be configured to model the interference signal at the fundamental frequency and the second, third, and fourth harmonics.

However, a skilled artisan will recognize a wide variety of signal modeling combinations from the disclosure herein.

Furthermore, the demodulation module 403B can be configured to model the full energy spectrum of the interference signal at the frequencies of interest. This can be accomplished by capturing the energy of the interference signal at the frequencies of interest regardless of the phase variation of the interference signal at those frequencies. In some embodiments, this can be accomplished by using both cosine and sine as demodulating signals. Because cosine and sine signals of the same frequency are $\pi/2$ radians out of phase, using these as complementary demodulating signals can model and capture all of the potential interference signal energy at the frequencies of interest. In some embodiments, the spectrum of the interference signal can be modeled by using only a cosine or only a sine demodulating signal. A skilled artisan will recognize a wide variety of demodulating signals, such as orthogonal signals, from the disclosure herein.

As is illustrated in FIG. 4B, the demodulation module 403B can model the full spectrum of the interference signal at the fundamental frequency $F_o$ and the harmonics $2F_0$, $3F_0$, and $4F_0$. Both sine and cosine demodulating signals can be used. The digitized composite detector signal $x_k(n)$ 401B can be multiplied by $\sin(2\pi F_0/F_s n)$ at 410 and by $\cos(2\pi F_0/F_s n)$ at 420 to model the full spectrum of the interference signal at the fundamental frequency $F_0$ ($F_s$ is the sampling frequency). The digitized composite detector signal $x_k(n)$ 401B can be multiplied by $\sin(4 \pi F_0/F_s n)$ at 430 and by $\cos(4 \pi F_0/F_s n)$ at 440 to model the full spectrum of the interference signal at the second harmonic $2F_0$. The digitized composite detector signal $x_k(n)$ 401B can be multiplied by $\sin(6 \pi F_0/F_s n)$ at 450 and by $\cos(6 \pi F_0/F_s n)$ at 460 to model the full spectrum of the interference signal at the third harmonic $3F_0$. Finally, the digitized composite detector signal $x_k(n)$ 401B can be multiplied by $\sin(8 \pi F_0/F_s n)$ at 470 and by $\cos(8 \pi F_0/F_s n)$ at 480 to model the full spectrum of the interference signal at the third harmonic $4F_0$. As is illustrated, N=8 channels of demodulated interference signal data can be produced.

The demodulated interference signal data can be presented to a decimation module 404B, which reduces the sampling rate by eliminating samples and, additionally, may provide signal conditioning and filtering. Because decimation reduces the number of data samples, it can reduce computational burden on the interference detector 440B and, additionally, reduce power consumption of the patient monitor. As is illustrated in FIG. 4B, the decimation module 404B can be configured as a series of downsample-by-2 blocks, each of which reduces the sampling rate by a factor of 2 by discarding every other signal sample. In order to satisfy the sampling theorem and to avoid aliasing, each of the downsample-by-2 blocks should be preceded by a low-pass filter having a cutoff frequency of $F_s/2^m$, where m is the number of the downsample-by-2 block in the series. Performing the low-pass filtering can result in the elimination of the components at other higher frequencies that do not carry any potentially useful information after the demodulation has been performed. Accordingly, the first channel of demodulated interference signal data (after being multiplied by $\sin(2\pi F_0/F_s n)$ at 410) can be filtered at 411 by a low-pass filter having a cut-off frequency of $F_s/2$, and can be subsequently decimated by a factor of 2 at 412. Subsequently, the remaining data samples of the first channel can be similarly filtered and decimated until, after being filtered by a low-pass filter 413 having a cut-off frequency of $F_s/2^m$ and decimated by a factor of 2 by a downsample-by-2 block at 414, the data samples are reduced to the desired sampling rate. This performed for each channel of demodulated interference signal data, as is illustrated in FIG. 4B. In some embodiments a 48 KHz demodulated multiple channel data stream can be decimated to 62.5 Hz by a string of $\log_2(48000/62.5)$ (or approximately 10) downsample-by-2 blocks, each preceded by an anti-aliasing low-pass filter. In some embodiments downsample-by-M blocks can be used instead, each of which reduces the sampling rate by a factor of M. In some embodiments (e.g., when a sigma-delta analog-to-digital converter is used), downsample-by-L and downsample-by-M blocks can be used instead, each of which reduces the sampling rate by a factors of L and M. In some embodiments, a single downsample block can be used to achieve the desired sampling rate. A skilled artisan artisan will recognize a wide variety of signal decimation techniques from the disclosure herein.

The demodulated, decimated interference signal data can be presented to an energy detector 405B for calculation of interference levels. A signal's energy can be calculated by summing up squared absolute values of the signal samples. As is illustrated in FIG. 4B, the demodulated, decimated data samples of the first channel are squared at 415. This can be performed for each channel of demodulated, decimated interference signal data. In some embodiments, the squared samples can be summed up. In some embodiments in addition to being summed up, the squared samples can also be filtered by a moving average filter. A moving average filter has low-pass characteristics and, accordingly, smoothes the signal by removing high-frequency components (e.g., short ambient or environment noise transients). A moving average filter can be configured with weighted or non-weighted filter coefficients. For example, a simple, non-weighted moving average filter sums up all the squared samples and divides the resulting sum by the number of samples. This results in computing the average power of the signal. As is illustrated in FIG. 4B, the calculated energy signal of the first channel is smoothed by the moving average filter 416 to determine the average power (or simply power) of the signal. As is illustrated, this can be performed on each channel of demodulated, decimated data to determine the power of the interference signal on each channel. In some embodiments, root mean square power of the signal on each channel can be computed by further calculating a square root of the computed power.

In some embodiments, the calculated energy or power computed for complementary cosine and sine channels sharing the same frequency can be summed in order to determine energy or power of the interference signal at each frequency of interest. As is explained above, because cosine and sine signals of the same frequency are $\pi/2$ radians out of phase, using both as complementary demodulating signals can model and capture all of the potential interference signal energy at the frequencies of interest. As is illustrated in FIG. 4B, at 490 the computed power values are added up in order determine the full spectrum power of the interference signal at the fundamental frequency $F_0$. Similar additions can be performed on other channels in order to determine the full spectrum power of the interference signal at the second ($2F_0$), third ($3F_0$), and fourth ($4F_0$) harmonics.

The interference level (or output) computed by the interference detector 440B for the digitized composite detector signal $x_k(n)$ 401B can be the maximum computed energy or power at the frequencies of interest. As is illustrated in FIG. 4B, at 495 such maximum can be selected as the output of the interference detector 440B. The maximum computed signal energy or power of the interference signal can represent the worst-case conditions for measuring physiological parameter information. In some embodiments, all computed interference signal energies or powers can be output. In some embodiments, the computed values can be further processed, such as averaged, filtered, and the like. A skilled artisan will recognize a wide variety of approaches to compute the interference output from the disclosure herein.

Figure 4C:
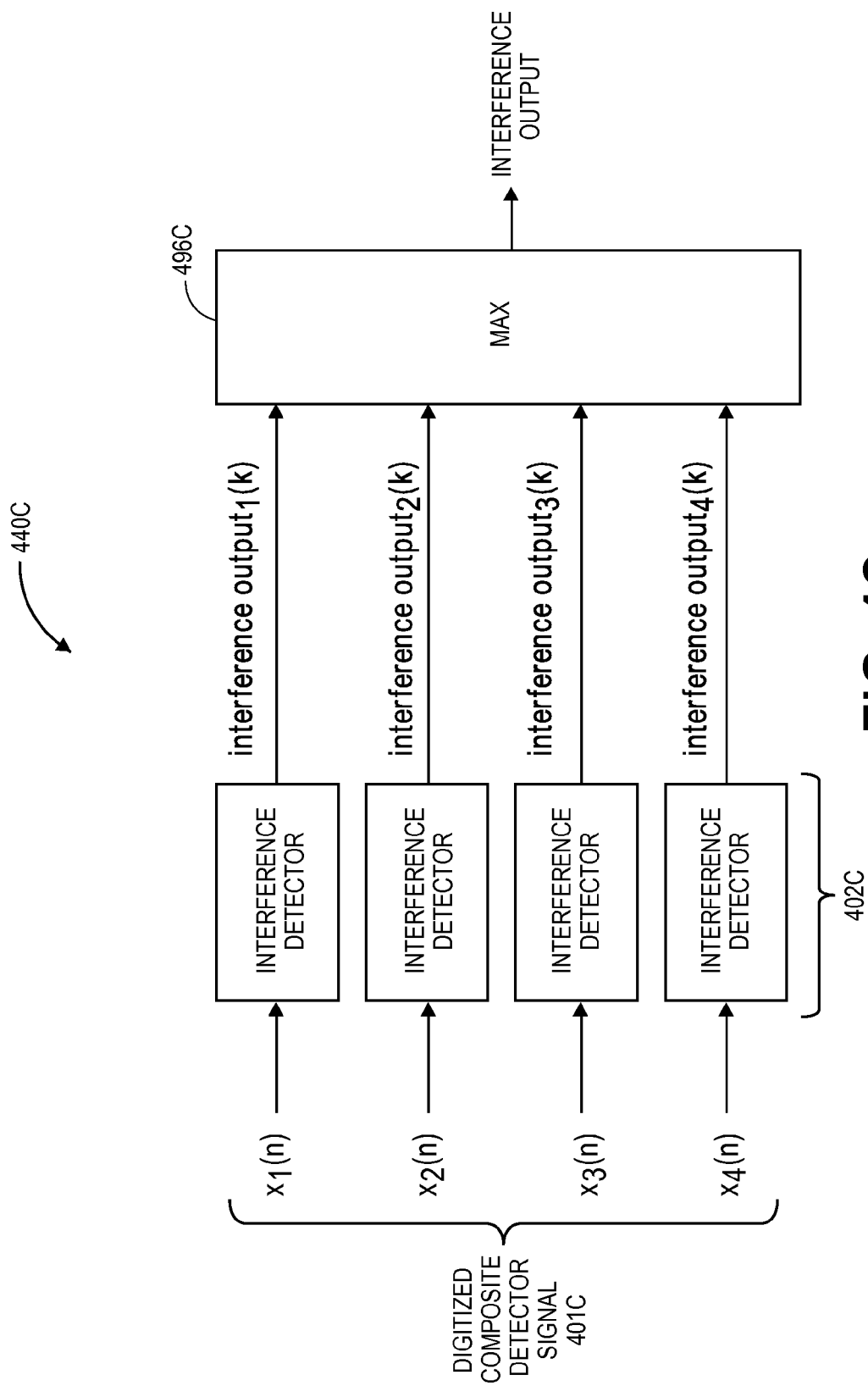

FIG. 4C illustrates a functional block diagram of an interference detector 440C of the patient monitor, such as, for example, the processor 428 of FIG. 4A. In embodiments comprising multiple detectors 206, computation of the interference levels can be performed separately on each composite detector signal captured by each of the detectors 206. As is shown in FIG. 4C, the interference detector 440C comprises four interference detectors 402C, each configured for calculating the interference level for the composite detector signal, $x_1(n)$ through $x_4(n)$, obtained from each of four detectors 206. Each of the interference detectors 402C can be configured as the detector 440B of FIG. 4B, and can output the maximum computed interference signal energy or power. At 496C, the maximum interference signal energy (or power) can be selected as selected as output. This can represent the worst-case conditions for measuring physiological parameter information. In some embodiments, all computed interference signal energies or powers can be output. In some embodiments, the computed values can be further processed, such as averaged, filtered, and the like. A skilled artisan will recognize a wide variety of approaches to compute the interference level from the disclosure herein.

FIG. 5 illustrates an interference detection process performed by a patient monitoring system, such as the patient monitoring system 200 of FIG. 2. At step 501 the analog composite detector signal is received from the detector(s) 206. The signal can be configured to comprise only the interference signal without any light intensity components. At step 502, the composite detector signal is conditioned by, for example, adjusting or normalizing the signal's gain, removing unwanted frequency components by passing the signal through a band-pass or a low-pass filter, normalizing the phase of the signal by passing it through an all-pass filter with the desired phase response, and the like. At step 503, the conditioned composite detector signal is digitized into samples by performing ND conversion. At step 504, the digitized composite detector signal is demodulated into one or more data channels. Demodulated signal data can be obtained by shifting the frequency spectrum of the digitized composite detector signal to frequencies and phases of interest, by, for example, multiplying by cosine and/or sine functions of the desired frequency and phase. At step 505, the demodulated signal channels can be compressed by decimation. Decimation reduces the number of samples comprised by each channel. Also, in order to avoid aliasing of the channel data, decimation should be preceded by low-pass filtering and removing unwanted higher frequency components from the channels. At 506, the energy of the digitized composite detector channel data is determined. For example, this can be accomplished by calculating the power of the signal on each channel by summing up the squared values of samples on each channel and dividing by the number of samples. In some embodiments, the maximum computed power is selected across all channels to determine the worst-case (i.e. maximum) power of the detected interference signal.

The maximum computed energy or power of the interference signal (or interference output) can be communicated to the user at 507. In some embodiments, the interference output can be presented to the user visually as, for example, in a bar graph. As is illustrated in FIG. 5, the interference output can be compared to a threshold. In some embodiments, the threshold can be configured as a multiple of the noise floor of the patient monitoring system. The noise floor of a system is a measure of the noise signal created inherently (i.e., without application of any input signal) by the electronic components of the system due to thermal noise, shot noise, and the like. The noise floor further establishes a limit on the smallest measurement that can be reliably performed by the system. Furthermore, the noise floor of a system can be measured experimentally. For example, the noise floor of a system for measuring the concentration of total hemoglobin in blood, such as 10 ppm. Accordingly, the threshold can be set according to the type of physiological parameter the patient monitoring system is configured to measure. In some embodiments, the threshold multiplier can be configurable and programmable.

As is illustrated in FIG. 5, at 510 the interference output can be compared to the threshold. When the interference output is smaller or equal to the threshold, the bar graph can be updated at 511 with green color (or shading) of height or width proportional to the threshold. For example, the height or width of the green bar can be computed as (threshold−interference output)/threshold. As another example, the computed value can be expressed as a percentage. When the interference output is greater than the threshold, the bar graph can be updated at 512 with red color (or shading) of height or width proportional to the threshold. For example, the height or width of the red bar can be computed as (interference output−threshold)/threshold. As another example, the computed value can be expressed as a percentage. A skilled artisan will recognize that other computation formulas or colors can be used to alert the user to the interference output of the patient monitor.

Figure 6A:
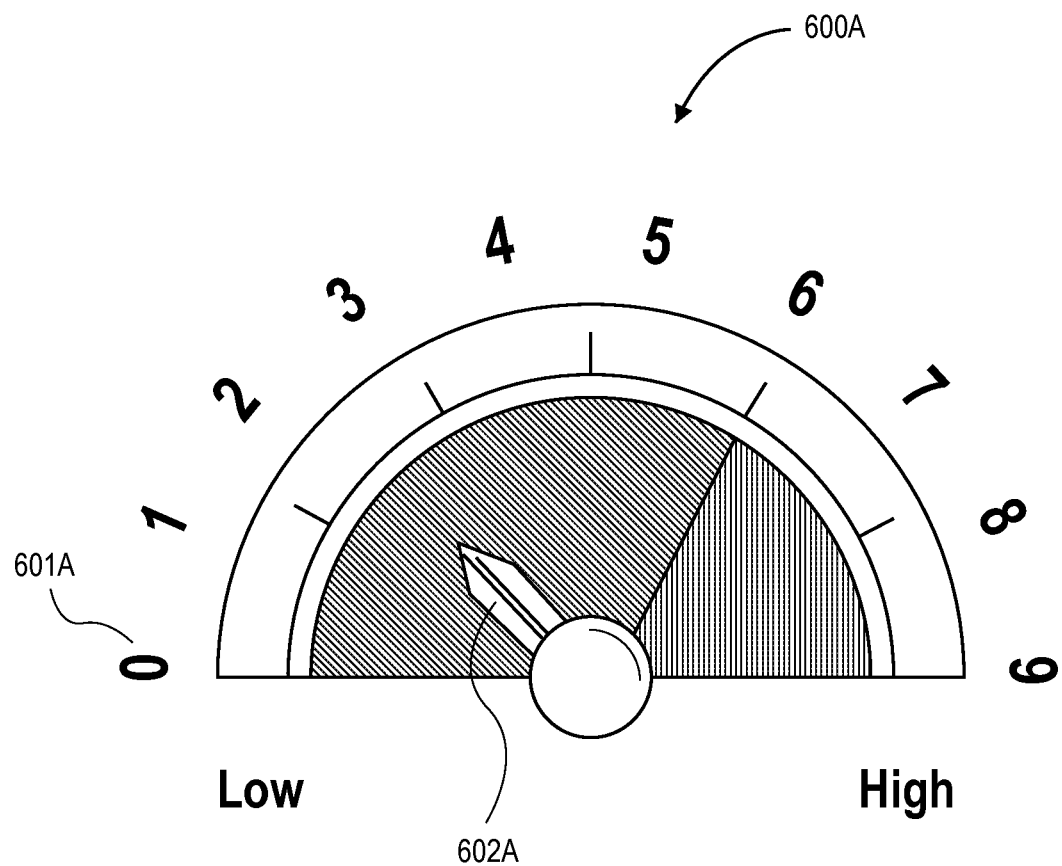

FIGS. 6A-D illustrate user interface indicia indicating use of and output from the interference detector, such the interference detector of FIG. 1. FIG. 6A illustrates a speedometer gauge-type visual display 600A of the calculated interference output. The dial 601A comprises numbers (0-9) indicating the severity of the interference output. The threshold can, for example, correspond to approximately the middle of the dial (i.e. number 6). The arrow 602A is configured to point to the calculated interference output relative to the threshold. The dial can be further shaded to for quick visual indication of the severity of the calculated interference output. For example, the shading under the range 0-3 can be green to indicate low interference levels, the shading under the range 3-6 can be yellow to indicate moderate interference levels, and the shading under the range 6-9 can be red to indicate severe interference levels.

FIG. 6B illustrates a bar graph-type visual display 600B. The green color or shading 603B indicates the percentage of the computed interference output relative to the threshold. For example, when the threshold is 10 and the computed interference output is 2, the green color or shading 603B can display 80% (i.e., 100%×(10−2)/10) and its width can be indicative of this percentage value. The red color or shading 604B likewise indicates the percentage of the interference output relative to the threshold. In the above example, the red color or shading 604B can display 20% and its width can be indicative of this percentage value. Alternatively, the red color or shading may not be displayed unless the computed interference output exceeds the threshold. For example, when the threshold is 10 and the computed interference output is 20, the red color or shading 604B can display 200% (i.e. 100%×20/10) with the width covering the entire bar graph display 600B. The green color or shading 603B may not be displayed in this case. In some embodiments, the threshold can correspond to the middle of the bar graph display 600B and the green and red color or shading can be computed and displayed accordingly. In some embodiments, other colors (e.g., yellow) can be also displayed.

FIG. 6C illustrates a bar graph-type visual display 600C. The green color or shading indicates the percentage of the computed interference output relative to the threshold, without displaying the percentage value. For example, when the threshold is 10 and the computed interference output is 6, the green color or shading 605C can be displayed with a width of 40% (i.e., 100%×(10−6)/10) of the bar graph display 600C. The red color or shading 606C likewise indicates the percentage of the interference output relative to the threshold. In the above example, the red color or shading 606C can be displayed with a width of 60%. Alternatively, the red color or shading may not be displayed unless the computed interference output exceeds the threshold. For example, when the threshold is 10 and the computed interference output is 11, the red color or shading 606C can be displayed with a width of 110% (i.e. 100%×11/10) or covering the entire bar graph display 600C. The green color or shading 605C may not be displayed in this case. In some embodiments, the threshold can correspond to the middle of the bar graph display 600C and the green and red color or shading can be computed and displayed accordingly. In some embodiments, other colors (e.g., yellow) can be also displayed.

FIG. 6D illustrates a bar graph-type visual display 600D which is similar to 600C but is vertical. The green color or shading indicates the percentage of the computed interference output relative to the threshold, without displaying the percentage value. For example, when the threshold is 10 and the computed interference output is 3, the green color or shading 607D can be displayed with a height of 70% (i.e., 100%×(10−3)/10) of the bar graph display 600D. The red color or shading 608D likewise indicates the percentage of the interference output relative to the threshold. In the above example, the red color or shading 608D can be displayed with a height of 40% of the bar graph display 600D. Alternatively, the red color or shading may not be displayed unless the computed interference output exceeds the threshold. For example, when the threshold is 10 and the computed interference output is 12, the red color or shading 608D can be displayed with the height of 120% (i.e. 100%×12/10) or covering the entire bar graph display 600D. The green color or shading 607D may not be displayed in this case. In some embodiments, the threshold can correspond to the middle of the bar graph display 600D and the green and red color or shading can be computed and displayed accordingly. In some embodiments, other colors (e.g., yellow) can be also displayed. FIGS. 6E-6H also illustrate alternative displays utilizing different colors, graphics, shapes and indications, including, for example, happy or sad faces, indicator bars, indicator lights, etc.

In some embodiments, the patient monitor can be configured to provide audio notification to the user. For example, after computing the interference output and comparing it to the threshold, the patient monitor can sound the phrase "Safe to Measure" when the interference output is below the threshold. As another example, the patient monitor can sound the phrase "Danger" when the interference output is close or above the threshold. A skilled artisan will recognize a variety of audio/visual notification techniques from the disclosure herein.

Although the interference detector for a patient monitor is disclosed with reference to its preferred embodiment, the invention is not intended to be limited thereby. Rather, a skilled artisan will recognize from the disclosure herein a wide number of alternatives for the interference detector for patient monitor. For example, the patient monitor can "lock out" the user from performing measurements of physiological parameters when the computed interference levels are determined to significantly degrade the accuracy of the measurements.

In addition to those processes described above, other processes and combination of processes will be apparent to those of skill in the art from the present disclosure. Those of skill will further appreciate that the various illustrative logical blocks, modules, and steps described in connection with the embodiments disclosed herein may be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

The various illustrative logical blocks, modules, and steps described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The modules can include, but are not limited to, any of the following: software or hardware components such as software, object-oriented software components, class components and task components, processes, methods, functions, attributes, procedures, subroutines, segments of program code, drivers, firmware, microcode, circuitry, data, databases, data structures, tables, arrays, or variables.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. It is contemplated that various aspects and features of the invention described can be practiced separately, combined together, or substituted for one another, and that a variety of combinations and subcombinations of the features and aspects can be made and still fall within the scope of the invention. Furthermore, the systems described above need not include all of the modules and functions described in the preferred embodiments. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A noninvasive monitor for determining measurement values for one or more physiological parameters of a monitored patient, the noninvasive monitor comprising:
    an input configured to receive from a sensor one or more sensor signals responsive to optical radiation, said sensor including an optical radiation source and one or more detectors housed in a sensor housing configured to position said optical radiation source and said one or more detectors proximate tissue of a patient; and
    a processor configured to:
        process a first sensor signal of said one or more sensor signals to determine measurement values for one or more physiological parameters of said patient, said first sensor signal responsive to optical radiation attenuated by said tissue of said patient,
        process a second sensor signal of said one or more sensor signals to determine an amount of ambient electronic interference proximate said sensor, said second sensor signal responsive to ambient electronic interference proximate said sensor, and
        output an output signal responsive to said amount of ambient electronic interference to provide at least a visual cue on an analog gauge indicative of said amount of ambient electronic interference.

2. The noninvasive monitor of claim 1, wherein said processor is configured to output said output signal to provide said visual cue relative to ranges of ambient electronic interference.

3. The noninvasive monitor of claim 2, wherein said ranges of ambient electronic interference include a first range associated with a low severity of ambient electronic interference, a second range associated with a medium severity of ambient electronic interference, and a third range associated with a high severity of ambient electronic interference.

4. The noninvasive monitor of claim 1, further comprising an analog display configured to display said visual cue.

5. The noninvasive monitor of claim 1, further comprising a digital display configured to display said visual cue.

6. The noninvasive monitor of claim 1, wherein said input is configured to receive said first sensor signal at a different time than when said input receives said second sensor signal.

7. The noninvasive monitor of claim 1, further comprising a sound transducer configured to output an audio cue responsive to said output signal.

8. The noninvasive monitor of claim 1, wherein said processor is configured to compare said amount of ambient electronic interference to a threshold to determine a suitability of a testing environment for patient monitoring.

9. The noninvasive monitor of claim 8, wherein said processor is configured to vary said threshold according at least to said one or more physiological parameters monitored for said patient.

10. The noninvasive monitor of claim 1, wherein said second sensor signal is responsive to ambient electronic interference proximate said sensor after attenuation by said tissue of said patient.

11. A method of testing an environment to be suitable for patient monitoring with a sensor including an optical radiation source and one or more detectors housed in a sensor housing, said sensor housing configured to position said optical radiation source and said one or more detectors proximate tissue of a patient, said sensor configured to output a sensor signal responsive to optical radiation attenuated by said tissue of said patient, the method comprising:
    receiving from a sensor, at an input, one or more sensor signals responsive to optical radiation, said one or more sensor signals including a sensor signal responsive to ambient electronic interference proximate said sensor;
    electronically processing said sensor signal responsive to ambient electronic interference proximate said sensor to determine an amount of ambient electronic interference proximate said sensor; and
    outputting an output signal responsive to said amount of ambient electronic interference to provide at least a visual cue indicative of said amount of ambient electronic interference.

12. The method of claim 11, further comprising comparing said amount of ambient electronic interference to a threshold to determine a suitability of a testing environment for patient monitoring.

13. The method of claim 11, further comprising:
    determining said amount of ambient electronic interference at a first location; and
    in response to determining that said first location is not a suitable testing environment for determining measurement values for one or more physiological parameters of a patient, determining said amount of ambient electronic interference at a second location different from said first location.

14. The method of claim 11, further comprising:
    determining levels of interference of said amount of ambient electronic interference at a plurality of frequencies; and
    determining a likelihood of successful processing of at least some of said one or more sensor signals given said amount of ambient electronic interference.

15. The method of claim 11, wherein said one or more sensor signals comprise a sensor signal responsive to optical radiation attenuated by tissue of a patient, and further comprising electronically processing said sensor signal responsive to optical radiation attenuated by said tissue of said patient to determine measurement values for one or more physiological parameters of said patient.

16. The method of claim 15, wherein said sensor signal responsive to ambient electronic interference proximate said sensor is responsive to ambient electronic interference proximate said sensor after attenuation by said tissue of said patient.

17. A noninvasive monitor configured to test a suitability of an environment for patient monitoring with a sensor including an optical radiation source and one or more detectors housed in a sensor housing, said sensor housing configured to position said optical radiation source and said one or more detectors proximate tissue of a patient, the noninvasive monitor comprising:

an input configured to receive from a sensor one or more sensor signals responsive to optical radiation, said one or more sensor signals including a sensor signal responsive to ambient electronic interference proximate said sensor; and a processor configured to:
   determine an amount of ambient electronic interference proximate said sensor based at least on said sensor signal responsive to ambient electronic interference proximate said sensor, and
   output at least one of an audio or visual indication of said amount of ambient electronic interference.

18. The noninvasive monitor of claim 17, wherein said processor is further configured to compare said amount of ambient electronic interference to a threshold to determine a suitability of a testing environment for patient monitoring.

19. The noninvasive monitor of claim 18, wherein said processor is configured to vary said threshold according at least to one or more physiological parameters monitored for a patient.

20. The noninvasive monitor of claim 17, wherein said processor is configured to determine levels of interference of said amount of ambient electronic interference at a plurality of frequencies and determine a likelihood of successful processing of at least some of said one or more sensor signals given said amount of ambient electronic interference.

21. The noninvasive monitor of claim 17, wherein said processor is configured to output said visual indication so that said visual indication is shown relative to ranges of ambient electronic interference.

22. The noninvasive monitor of claim 17, wherein said one or more sensor signals comprise a sensor signal responsive to optical radiation attenuated by tissue of a patient, and wherein said processor is configured to determine measurement values for one or more physiological parameters of said patient based at least on said sensor signal responsive to optical radiation attenuated by said tissue of said patient.

* * * * *